United States Patent [19]

Schrader

[11] 4,018,186

[45] Apr. 19, 1977

[54] GAUZE IMPREGNATOR

[76] Inventor: Charles E. Schrader, 8536 Oak Park Ave., Northridge, Calif. 91325

[22] Filed: May 5, 1975

[21] Appl. No.: 574,439

[52] U.S. Cl. ............................................ 118/405
[51] Int. Cl.[2] ...................................... B05C 3/12
[58] Field of Search .......... 118/404, 405, 415, 428; 68/18 R, 195, 175; 427/434 E, 177–179

[56] References Cited

UNITED STATES PATENTS

| 102,893 | 5/1870 | Warth et al. | 118/405 X |
| 287,776 | 10/1883 | Phillips | 118/405 X |
| 752,458 | 2/1904 | Lehman | 118/405 X |
| 1,794,039 | 2/1931 | Silvano et al. | 118/405 X |
| 3,064,459 | 11/1962 | Messinger | 68/175 |
| 3,084,662 | 4/1963 | Badger | 118/404 X |
| 3,681,949 | 8/1972 | Fleissner | 68/181 R |

FOREIGN PATENTS OR APPLICATIONS

| 451,793 | 10/1948 | Canada | 118/404 |

Primary Examiner—Morris Kaplan
Attorney, Agent, or Firm—Fuswider, Patton, Reiber, Lee & Utecht

[57] ABSTRACT

A machine for impregnating a fabric of woven fibers with a viscous liquid. The machine comprises a chamber to contain the medication, first and second slots in opposite sidewalls of the chamber with overlying, first and second, resilient seals carried on the walls of the chamber and bearing fabric-receiving slits. The machine is provided with a supply roll of a continuous band of fabric, e.g., medical gauze, and a motorized take-up spindle whereby a continuous strip of gauze can be passed through the slits of the seals and the chamber, and be impregnated with the viscous ointment within the chamber. Preferably, the chamber carries a platform plate at the level of the slits and a plurality of apertures are provided in the platform plate. The band of fabric or gauze is directed through the chamber and over the surface of the platform plate so that during its passage through the chamber the viscous material within the chamber will be extruded into the open, porous weave of the fabric or gauze.

15 Claims, 15 Drawing Figures

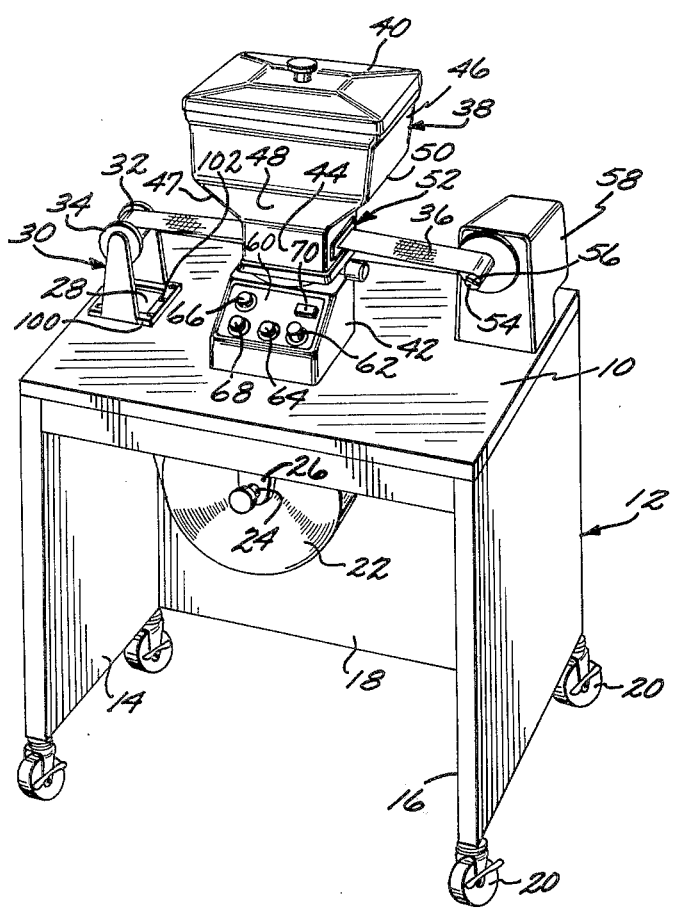

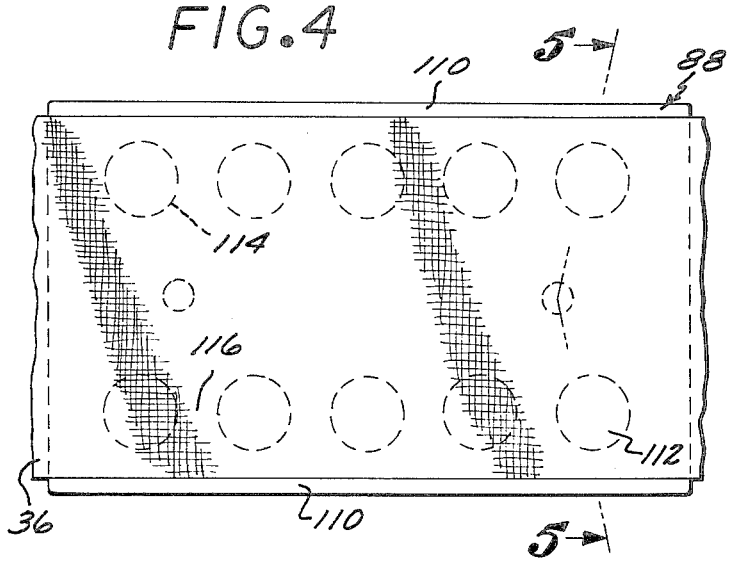
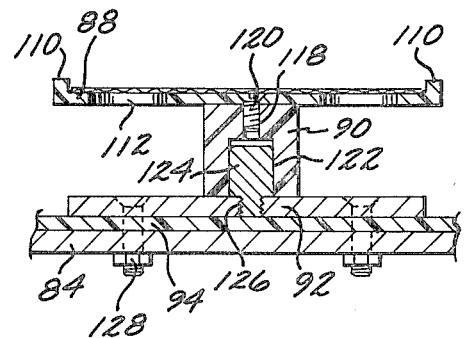
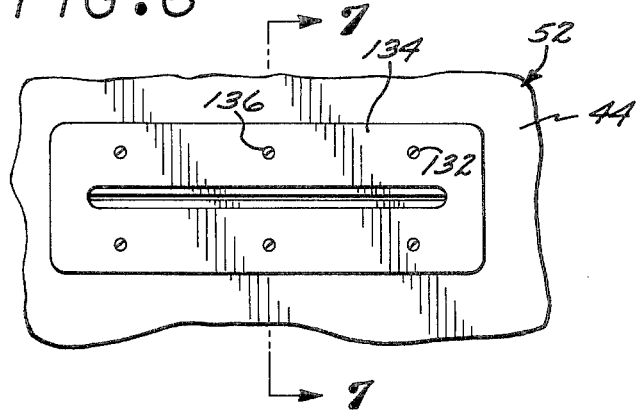
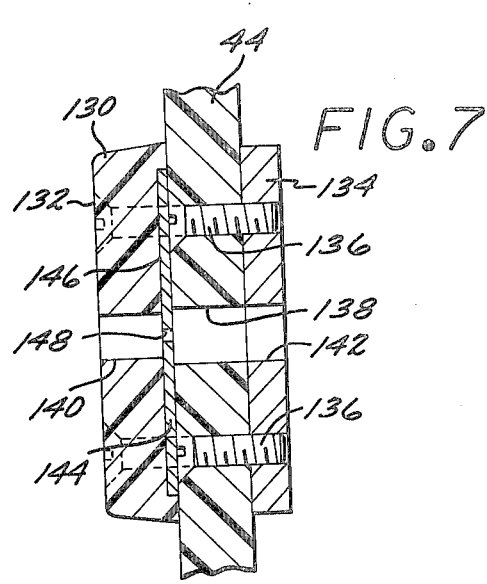
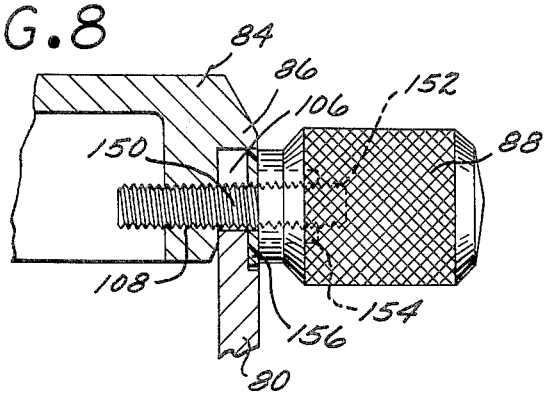
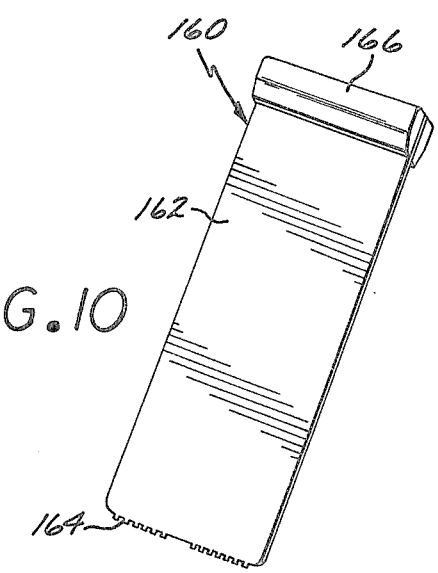
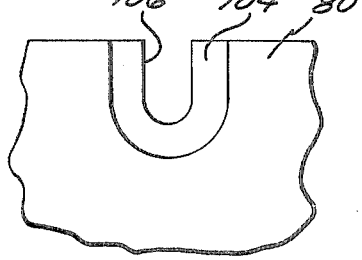

GAUZE IMPREGNATOR

BACKGROUND OF THE INVENTION

1. Field of the invention

This invention relates to an apparatus for impregnation of fabric and, particularly, relates to an apparatus for the impregnation of a band of fabric such as medical gauze with a viscous medication in the preparation of rolled bandages.

2. Brief Statement of the Prior Art

Burn victims are commonly treated by covering the burn areas entirely with gauze bandages, thereby excluding exposure to air. The bandages are saturated or impregnated with various antiseptic ointments and medications to prevent infections from developing in the affected areas. A material recently approved for use as a burn medication is silver sulfadiazine, marketed under the tradename Silvidene by Marrion Laboratories, 10236 Bunker Ridge Road, Kansas City, Mo. This material is of a highly viscous, semisolid consistency, similar to that of hand creams and ointments.

Difficulties are experienced when attempting to thoroughly impregnate or saturate the open pores of medical gauze with this material. The gauze is commonly employed in widths of approximately 3 inches, which are the optimum size for holding in the palm of the physician or nurse while wrapping limbs of the victim. For successful application, the medication should be impregnated in the pores of the gauze to impart tackiness thereto, thereby facilitating the application of the bandage to the patient. The material should not, however, be applied to the bandage in excess since the excess material will extrude from the gauze as it is rolled onto the take-up spindle, requiring frequent cleanup of the apparatus and loss of valuable medication.

It is, therefore, desirable to provide an apparatus for the impregnation of continuous lengths of medical gauze with highly viscous medications. Preferably, the apparatus should be supplied with suitable operation controls whereby the operator can preselect lengths of continuous gauze to be impregnated for the preparation of bandages of varied and preselected length.

BRIEF STATEMENT OF THE INVENTION

This invention comprises an apparatus for the continuous impregnation of medication into the open pores of fabrics of woven fibers such as sterile, medical gauze and the like.

The device comprises a chamber for holding a supply of the medication, first and second slots in opposite sidewalls of the chamber with first and second resilient seal means carried on the sidewalls of the chamber and overlying the slots. The apparatus is provided with a motorized take-up spindle and means for the removable mounting of a supply roll of a continuous length of woven fabric such as medical gauze in a position to supply a continuous band of the gauze through the slits of the resilient seal means, through the chamber and onto the take-up spindle. To insure that the fabric is completely impregnated with the medication during its passage through the chamber, the fabric is passed over a platform plate supported within the chamber approximately at the level of the slits. A plurality of apertures are provided in the platform whereby the medication can continuously wick through the apertures and into contact with the fabric passing over the plate. The passage of the material over the plate serves to effect extrusion of the surrounding viscous material into the open pores of the woven gauze and obtain complete impregnation of the gauze with the medication.

The width of the slit in the resilient seals is sufficient to wipe excess material from the surface of the gauze as it exits the chamber. The motorized take-up spindle is provided with suitable circuit control facilities whereby the operator can preselect a desired length of bandage and the machine will stop the advance of the gauze when the preselected length is attained on the take-up spindle. Preferred embodiments of the invention include facilities retaining the resilient seal means on the exterior walls of the chamber, overlying the slots in the chamber walls so that the resilient seal means can be replaced without disturbing the contents of the chamber.

BRIEF DESCRIPTION OF THE DRAWINGS

The invention will be described by reference to the drawings of which:

FIG. 1 is the perspective view of the impregnating apparatus;

FIG. 2 is an end view of the apparatus;

FIG. 3 is a partial elevation sectional view along lines 3—3 of FIG. 2;

FIGS. 4 and 5 are views illustrating the platform plate carried within the medication chamber of the invention;

FIGS. 6 and 7 illustrate the resilient seal means and the mounting assembly permitting their removable attachment to the medication chamber of the invention;

FIGS. 8 and 9 illustrate the means for removable mounting of the medication chamber in the apparatus; and FIG. 10 illustrates the hand tool for feeding a band of gauze into and through the chamber of the apparatus.

BRIEF DESCRIPTION OF THE PREFERRED EMBODIMENTS

Referring now to FIG. 1, the fabric impregnating device of the invention is illustrated as carried on the table 10 of a mobile cart 12 having opposite sides 14 and 16, a closed back 18 and a plurality of caster wheels 20. The supply roll of a continuous band of a fabric such as gauze and the like is carried between distal disk guides 22 on a removable spindle 24 that is rotatably supported by a yoke member 26 secured to the undersurface of table 10. Table 10 is cut out at 28 to provide for mounting of an idler spindle assembly 30 carrying rotatably mounted idler spindles such as 32 with end disks 34 over which the continuous band of fabric 36 is passed.

The impregnating apparatus comprises a chamber 38 with removable cover 40 that is carried on a supporting pedestal secured to table 10 which surmounts the chamber 38 above the control unit housing 42. The preferred construction of chamber 38 is, as illustrated, with a base portion 44 of minor dimensions, a top portion 46 of major dimensions and tapered, transition sidewalls 47 – 50 therebetween. The walls are preferably tapered at inclined angles from the vertical of from about 20 to 60°, preferably 40 to about 50° to insure feeding of the viscous contents of the hopper to its lower base portion 44.

Opposite side walls in the base portion of the chamber 38 are slotted and bear seal means, generally indicated at 52, to permit passage of the continuous band 36 of fabric through the chamber 38.

The impregnated fabric exiting from chamber 38 is rolled about take-up spindle 52 which bears a longitudinal slit 56 for engagement with the forward end of the band of fabric. The spindle 54 is carried on the shaft turned by a motor contained within motor housing 58.

The control unit housing 42 bears a front panel 60 on which are mounted a plurality of controls such as dial knob 62 for setting a cycle to wind a preselected length of bandage about the take-up spindle 54, a switch button 64 for manual operation of the motorized take-up spindle, a start button 66 for starting the cycle to wrap a bandage of a preselected length and a stop button switch 68 for interrupting the cycle at any time. The panel is also provided with a master power switch 70.

Referring to FIG. 2, the general alignment of the various components of the invention can be seen. The motor housing 58 is generally mounted in line with the chamber 38 so that the continuous band of fabric 36 passes directly through the base portion 44 of chamber 38 and on to the take-up spindle 54. The take-up spindle bears a large diameter extractor ring 72 to facilitate removal of the rolled bandage from the take-up spindle. Ring 72 is slidably carried on the shaft 74 which extends into the motor housing and to mechanical linkage to the drive motor contained therein. The extractor ring 72 is carried on a Nylon bushing, not shown, which slides over shaft 54, thereby permitting its removal from the shaft.

Referring now to FIG. 3, the supply roll of the continuous band of fabric 36 is shown as carried by yoke 26 which is secured to the undersurface of table 10 by a plurality of fasteners such as conventional machine bolts 76. Preferably, these machine bolts extend through the table and through the base plate 78 of the supporting pedestal 80 for the chamber 38. The supporting pedestal 80 comprises a generally cylindrical or tubular member which is segmented along a portion of its length to provide an inset portion for receiving the control unit housing 42. The line of the segmented cut in supporting pedestal 80 is generally shown by the broken line 82 of FIG. 2. The upper portion of supporting pedestal 80 is cylindrical and receives an adaptor ring 84 which has a peripheral flange or rib 86 that surmounts the upper end of supporting pedestal 80. The ring 84 carries one or, preferably two, lock screws 88 that fixedly secure ring 84 to supporting pedestal 80.

Mounted within the base portion 44 of chamber 38 is a platform plate 88 that is carried by a plurality of block members 90 which extend from a base plate 92 secured to the bottom wall 94 of chamber 38. The slot and seal assemblies 52 carried on each of the opposite sidewalls base portion 44 are shown in FIG. 3 to permit passage of the continuous band of fabric 36 through the chamber and over platform plate 88.

The continuous band of fabric 36 unwrapped from the supply roll is passed over a lower idler spindle 96 that is carried at the lower end of opposite arms 98 of the idler assembly 30. Upright arms 98 are carried by a flat mounting plate 100 that overlies the cutout 28 in table 10 and that is secured thereto by suitable screw fasteners 102. The upper ends of support arms 98 bear rotatably mounted idler spindle 32 that is at a height slightly less than the elevation of the slots and seal assemblies 52 carried in the base portion 44 of chamber 38. The idler spindles such as 96 and 32 carry edge guides in the form of circular disks 32 to insure accurate tracking of the continuous band of fabric 36 across the spindles.

Referring now to FIGS. 4 and 5, the platform plate 88 will be described in greater detail. The plate 88 has longitudinal edge guides in the form of longitudinal ribs 110 that extend coextensively with plate 88. These edge guides 110 serve to restrain the continuous band of fabric 36 on the upper surface of plate 88. Plate 88 bears a plurality of apertures 112 which are spaced across its surface, preferably, in parallel rows 114 and 116.

Plate 88 is carried within chamber 38 on a plurality of support blocks 90 which are cylindrical caps having a central bore 118 which is threaded with internal threads to receive counter-sunk screw fasteners 120 for securing platform plate 88 thereto. The blocks 90 are counter-bored at 122 to provide a large diameter recess for surmounting on page 124 which are threadably secured in receiving bores 126 of face plate 92 at the bottom of chamber 38.

As previously mentioned, adaptor ring 84 is carried on the undersurface of chamber 38 and is secured to bottom wall 94 of this chamber by a plurality of fasteners such as bolts 128 which extend through the bottom wall 94 of the chamber and into engagement with bottom plate 92 mounted therein.

Referring now to FIGS. 6 and 7, the slot and seal assemblies 52 that are provided on opposite side walls in the base portion 44 of chamber 38 will be described in greater detail. As shown in FIG. 7, the exterior sidewall of base portion 44 carries a seal retaining plate 130 that is secured in the assembly by a plurality of screw fasteners 132 which extend through apertures in the sidewall of base portion 44 and into threaded engagement with internally threaded bores of backing plate 134 which is carried on the inside surface of the sidewall of base portion 44. The backing plate is secured to this sidewall by two screw fasteners 136 as shown in FIG. 6, which is a view of the backing plate 134 as it appears from the inside of base portion 44 of chamber 38.

The sidewall of the base portion 44 is slotted at 138 with a generally elongated slot of a length which is slightly greater than the width of the continuous band of fabric 36 to be passed through the chamber. Retaining plate 130 is similarly slotted at 140 and back-up plate 134 bears a similar slot 142. The seal in the assembly comprises a resilient, flexible membrane 144 that is carried in recess 146 of retainer plate 130 and is secured thereby to the exterior of the sidewall of base portion 44. The seal membrane 144 bears a thin slit 148 to receive the continuous band of fabric 36 and serves to seal the chamber 38 and prevent extrusion of the medication placed therein. The membrane 144 also controls the amount of material applied to the band of fabric 36 since it wipes the band passing through its slit 148. In this fashion, variation in the width of slit 148 can provide for variation in the amount of material impregnated onto the band of fabric 36.

Referring now to FIGS. 8 and 9, the means for fixedly securing the chamber 38 to the supporting pedestal 80 will be described. As previously mentioned, the adaptor ring 84 has a peripheral flange portion 86 which overlies the upper end of the supporting pedestal 80 to permit the adaptor ring 84 and surmounted chamber 38 to rest on the supporting pedestal 80. The adaptor ring 84 also bears a plurality of locking thumb screw 88 which are carried in threaded bores 108 in the skirt portion of adaptor ring 84. Corresponding open grooves 106 are provided in the top edge of supporting pedestal 80. Preferably, the supporting pedestal 80 is milled or ground to provide a flat shoulder 104 surrounding the open grooves 106. Grooves 106 receive the shaft of stud 150 which extends from its threaded engagement with bore 108 in adaptor ring 84 into engagement with a threaded bore 152 in thumb screw 88. A flanged bushing 154 bearing flange 156 is seated in a counter-bore in thumb screw 88, surrounding stud 150 to provide a binding engagement with flat 104 about open groove 106.

Means are also provided for threading the band of fabric 36 through the slits of the sealing membranes 144. To this end, the hand tool illustrated in FIG. 10 is provided. This tool 160 has a thin blade 162 of sheet metal that, preferably, bears a plurality of serrations or teeth 164 at its forward end and a handle 166 at its opposite end. When used, the end of the band of fabric 36 is looped over the serrated end of blade 162 and the blade 162 is passed through the slits 148 of the sealing membranes 144 to exit from the opposite side of the chamber 38 where the fabric can then be grasped by hand and passed over and unto the motorized take-up spindle 54.

A typical unit of the invention constructed for the impregnation of sterile gauze with a silver sulfadiazene medication employs a chamber 38 of approximately 4.5 gallons capacity. The gauze is of the size conventionally employed for treatment of burn victims and generally comprises a roll of continuous cotton or rayon fabric 3 inches wide and having an open weave. The splits in membranes 144 are provided with a thickness of about 0.017 inch, adequate to insure sealing of the chamber and prevention of extrusion of the medication through the slits during operation. The platform plate 88 is provided with two rows of five apertures of approximately 0.62 inches in diameter, adequate to insure sufficient wicking of the medication into contact with the underside of the gauze as it passes over platform plate 88. The motorized take-up spindle is powered by a conventional parallel shaft gear motor commercially available from Minarik Electric Co., 224 East 3rd Street, Los Angeles, Calif., equipped with a motor control Minarik Model SL14002 which utilizes an SCR triggered by a unijunction transistor. This circuit is provided with an externally adjustable speed control in the form of a potentiometer. The control circuit for the desired operation of the invention is connected to the aforedescribed motor control circuit through the external speed adjustment potentiometer leads across the terminals of a photosensitive transistor which is mounted to receive light from a light emitting diode. The light emitting diode circuit is controlled by a timing circuit having a pair of terminals connected across a capacitor. The charge rate of the capacitor is adjustable by the variable setting of the potentiometer by length control dial 62. When the capacitor is charged, the timing circuit is activated to remove the bias to a NPN switching transistor in the light emitting diode circuit, causing this transistor to switch into a non-conducting mode and switching the photosensitive transistor into a nonconducting mode, stopping operation of the motor. The manual stop cycle switch 68 is in a lead that shunts the capacitor. The manual operation switch 64 is in a shunt circuit across the terminals of the NPN switching transistor and includes a variable resistor to control the current flow through the light emitting diode to a level that would bias the photosensitiveness in a region where its conductance varies in linear proportion to the incident light from the light emitting diode thereby permitting fixed adjustability in the speed of the motor when under manual operation.

The materials employed in construction of the aforedescribed device include use of thermoplastic sheet material for the thermal forming of chamber 38. The thermoplastic material of preference is a commercially available, high strength grade of acrylonitrile-butadiene styrene copolymer. Various resilient and flexible plastics can be employed for the membrane seals such as Nylon-filled rubber, polyethylene, polyvinyl chloride; however, the preferred material for extended life is an ether base polyurethane which has a low moisture absorption and a high resistance to creep and deformation.

The aforedescribed apparatus is employed for the formation of gauze bandages, three inches wide by approximately nine feet in length. The dry weight of this length bandage is about 25 grams, and, after medication, the completed bandage weighs about 107 grams, a weight increase of 82 grams, corresponding to the impregnation of about 42 milligrams medication per square centimeter of gauze. At this concentration the gauze has the desired tackiness for use in treatment of burns but did not contain the excess quantities of the medication that would extrude from the bandage during its rolling on the take-up spindle.

The invention has been described with reference to the presently preferred embodiment thereof. It is not intended that the invention be unduly limited by the preceeding illustration and description. Instead, it is intended that the invention be defined by the means, and their obvious equivalents set forth in the following claims.

What is claimed:

1. An apparatus for the uniform impregnation of a viscous material into the open pores of a fibrous band at atmospheric pressure which comprises:
    a chamber charged with said viscous material;
    first and second slots in opposite side walls of said chamber open to atmospheric pressure;
    first and second resilient membrane seals overlying each of said slots and each bearing a fabric band receiving slit;
    means for removably supporting a roll of continuous fabric band and supplying said band to the first of said silts;
    spindle means for receiving said fabric band from the second of said silts and for winding said received band into a roll;
    and stationary platform plate means carried fixedly within and above the bottom of said chamber at the level of said slits and extending between said opposite side walls and bearing a plurality of apertures therethrough whereby said continuous fabric band can be passed between said slits, through said chamber and the viscous material and in contact with said plate means, to receive a uniform impregnation of viscous material contained within said chamber.

2. The apparatus of claim 1 wherein said viscous material is an ointment, medication and the like and said fibrous band is a woven fabric bandage.

3. The apparatus of claim 1 wherein said chamber has a base portion of minor dimensions, a top portion of major dimensions and tapered, transition side walls extending therebetween.

4. The apparatus of claim 3 wherein said chamber is formed of thermoformed plastics.

5. The apparatus of claim 1 wherein said chamber carries an interior base plate on its bottom surface that bears a plurality of support blocks on which is mounted said platform plate means.

6. The apparatus of claim 1 wherein said chamber is carried on a supporting pedestal and bears a bottom ring adaptor having a peripheral flange to rest on the upper edge of said supporting pedestal.

7. The apparatus of claim 6 wherein said chamber carries an interior base plate and said ring adaptor is secured to said chamber by a plurality of fasteners extending through the bottom of said chamber and into engagement with said base plate.

8. The apparatus of claim 6 wherein said supporting pedestal bears at least one open groove in its top edge and said ring adaptor carries a threadably received lock screw for the removable and fixed attachment of said chamber to said pedestal base.

9. The apparatus of claim 8 wherein said supporting pedestal bears a flat about said open groove to form a seat for said lock screw and wherein said lock screw bears a flanged bushing bearing against said flat.

10. The apparatus of claim 1 wherein said means for removably supporting a supply roll of fabric comprises yoke means carried on said apparatus and pivotally supporting shaft means having distal end disk guides.

11. The apparatus of claim 1 wherein said membrane seals are removably mounted on the exterior walls of said chamber to overlie the slots therein.

12. The apparatus of claim 11 including retaining plate means securing said membrane seals to the exterior walls of said chamber.

13. The apparatus of claim 12 wherein the interior walls of said chamber bear a backing plate secured thereto about said slot means and said retaining plate means are secured to said backing plate means by a plurality of threaded fasteners extending therebetween.

14. The apparatus of claim 1 including an extractor ring slidably mounted on said spindle means to facilitate removal of rolls of impregnated fabric bands therefrom.

15. The apparatus of claim 3 wherein said plate has opposite coextensive and longitudinal, raised edge guides to receive said fabric band therebetween.

* * * * *